(12) United States Patent
Hansen et al.

(10) Patent No.: US 12,344,625 B2
(45) Date of Patent: Jul. 1, 2025

(54) PROCESS FOR PREPARING RHENIUM CHELATED MAG3 OLIGONUCLEOTIDES

(71) Applicant: Roche Innovation Center Copenhagen A/S, Horsholm (DK)

(72) Inventors: Dennis Jul Hansen, Farum (DK); Erik Daa Funder, Hillerod (DK); Joerg Hoernschemeyer, Lorrach (DE)

(73) Assignee: Roche Innovation Center Copenhagen A/S, Horsholm (DK)

( * ) Notice: Subject to any disclaimer, the term of this patent is extended or adjusted under 35 U.S.C. 154(b) by 925 days.

(21) Appl. No.: 17/605,058

(22) PCT Filed: Apr. 28, 2020

(86) PCT No.: PCT/EP2020/061657
§ 371 (c)(1),
(2) Date: Oct. 20, 2021

(87) PCT Pub. No.: WO2020/221705
PCT Pub. Date: Nov. 5, 2020

(65) Prior Publication Data
US 2022/0194972 A1    Jun. 23, 2022

(30) Foreign Application Priority Data
Apr. 30, 2019 (EP) ................................. 19171953

(51) Int. Cl.
| | | |
|---|---|---|
| *C07F 13/00* | (2006.01) | |
| *A61K 51/04* | (2006.01) | |
| *C12N 15/113* | (2010.01) | |

(52) U.S. Cl.
CPC ........ *C07F 13/005* (2013.01); *A61K 51/0491* (2013.01); *C12N 15/113* (2013.01); *C12N 2310/3231* (2013.01); *C12N 2310/3517* (2013.01); *C12N 2320/30* (2013.01)

(58) Field of Classification Search
None
See application file for complete search history.

(56) References Cited

U.S. PATENT DOCUMENTS

| | | | |
|---|---|---|---|
| 4,861,869 A | 8/1989 | Nicolotti et al. | |
| 5,980,861 A | 11/1999 | Hnatowich et al. | |
| 6,127,530 A | 10/2000 | Duatti et al. | |
| 2011/0033379 A1 | 2/2011 | Frangioni et al. | |
| 2014/0271461 A1 | 9/2014 | Reb et al. | |

FOREIGN PATENT DOCUMENTS

| | | |
|---|---|---|
| JP | 63-001972 A | 1/1988 |
| JP | 2001-501616 A | 2/2001 |
| JP | 2015-029926 A | 2/2015 |
| JP | 2016-516707 A | 6/2016 |
| WO | 98/39352 A1 | 9/1998 |
| WO | 99/14226 A2 | 3/1999 |
| WO | 00/47599 A1 | 8/2000 |
| WO | 00/66604 A2 | 11/2000 |
| WO | 2004/046160 A2 | 6/2004 |
| WO | 2007/090071 A2 | 8/2007 |
| WO | 2007/134181 A2 | 11/2007 |
| WO | 2008/027995 A2 | 3/2008 |
| WO | 2008/150729 A2 | 12/2008 |
| WO | 2008/154401 A2 | 12/2008 |
| WO | 2009/006478 A2 | 1/2009 |
| WO | 2009/067647 A1 | 5/2009 |
| WO | 2010/036698 A1 | 4/2010 |
| WO | 2010/077578 A1 | 7/2010 |
| WO | 2011/017521 A2 | 2/2011 |
| WO | 2011/156202 A1 | 12/2011 |
| WO | 2013/154798 A1 | 10/2013 |

OTHER PUBLICATIONS

Office Action received for Japanese Patent Application No. 2021-564464, mailed on Dec. 28, 2023, 6 pages (3 pages of English Translation and 3 pages of Original Document).
Alsbaiee, A., et al., "Synthesis of rhenium chelated MAG3 functionalized rosette nanotubes", Tet. Lett., 53: 1645-1651 (2012).
Crudo, J.L., et al., "Optimization of antibody labeling with rhenium-188 using a prelabeled MAG3 chelate", International Journal of Pharmaceutics, 248: 173-182 (2002).
Deleavey, G.F., et al., "Designing Chemically Modified Oligonucleotides for Targeted Gene Silencing", Chemistry and Biology, 19(8): 937-954 (2012).
Freier, S.M., et al., "The ups and downs of nucleic acid duplex stability: structure-stability studies on chemically-modified DNA:RNA duplexes", Nucl. Acid Res., 25(22): 4429-4443 (1997).
Kimura, S., et al., "Synthesis and evaluation of a novel 99mTc-labeled bioreductive probe for tumor hypoxia imaging", Bioorganic and Medicinal Chemistry Letters, 21: 7359-7362 (2011).
Mitsuoka, Y., et al., "A bridged nucleic acid, 2',4'-BNA COC : synthesis of fully modified oligonucleotides bearing thymine, 5-methylcytosine, adenine and guanine 2',4'-BNA COC monomers and RNA-selective nucleic acid recognition", Nucleic Acids Research, 37(4): 1225-1238 (2009).
Morita, K., et al., "2'-O,4'-C-ethylene-bridged nucleic acids (ENA): highly nuclease-resistant and thermodynamically stable oligonucleotides for antisense drug", Bioorganic & Med.Chem. Lett., 12(1): 73-76 (2002).

(Continued)

*Primary Examiner* — Zinna Northington Davis
(74) *Attorney, Agent, or Firm* — Smith, Gambrell & Russell, LLP; Judy Jarecki-Black; Sharon Ngwenya

(57) ABSTRACT

The present invention relates to a novel process for preparing a compound of formula (III) and rhenium chelated MAG3 oligonucleotides.

(III)

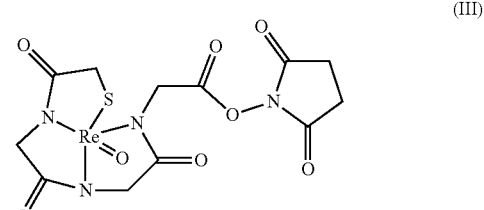

17 Claims, No Drawings

(56) References Cited

OTHER PUBLICATIONS

Seth, P.P., et al., "Synthesis and Biophysical Evaluation of 2',4'-Constrained 2'O-Methoxyethyl and 2',4'-Constrained 2'O-Ethyl Nucleic Acid Analogues", J. Org. Chem., 75(5): 1569-1581 (2010).
Uhlmann, E., "Recent advances in the medicinal chemistry of antisense oligonucleotides", Curr. Opinion in Drug Development, 3(2): 203-213 (2000).
Winnard, P., et al., "Preparation and use of NHS-MAG3 for technetium-99m labeling of DNA", Nuclear Medicine & Biology, 24: 425-432 (1997).

PROCESS FOR PREPARING RHENIUM CHELATED MAG3 OLIGONUCLEOTIDES

CROSS REFERENCE TO RELATED APPLICATIONS

This application is a national stage application, filed under 35 U.S.C. § 371, of International Patent Application No. PCT/EP2020/061657 filed on Apr. 28, 2020, which claims benefit of and priority to European Patent Application No. 19171953.3 filed on Apr. 30, 2019, which are incorporated herein by reference in their entirety.

The invention relates to a novel process for preparing rhenium chelated MAG3 (mercaptoacetyltriglycine) as well as rhenium chelated MAG3 oligonucleotides.

Rhenium (Re) and technetium (Tc) have shown significant potential in nuclear medicine due to the prospective applications of rhenium radionuclides 186Re and 188Re in therapeutic nuclear medicine and technetium radionuclide 99mTc in medical diagnostic imaging. 186Re and 188Re radionuclides are both γ and β-emitting agents, while 99mTc radionuclide is only a γ-emitting agent; they exhibit favorable nuclear properties for medical imaging and therapy. Rhenium and technetium based radiopharmaceuticals are widely applied in medical diagnostic imaging and therapeutic nuclear medicine in Europe and other parts of the world The MAG3 ligand is a well-established imaging ligand which forms a stable metal complex with rhenium (Re) or technetium (Tc). Many different bioactive molecules such as sugars, siRNA and antisense oligonucleotides to only name a few, have been functionalized with MAG3. The resulting Re or Tc complexes may be of medical significance in the field of radiopharmacy, since radioactive isotopes such as 186Re or 188Re are used for the diagnosis or treatment of tumors or renal function. But fundamental research is still necessary for the attachment of radiometals to biologically active molecules. Most rhenium(V)-based radiopharmaceuticals lack stability (at physiological conditions) or selectivity (in terms of targeting cells, or in terms of preparing an exactly defined agent) and their synthesis remain to be improved.

For instance, Alsbaiee et al. describe the synthesis of rhenium chelated MAG3 functionalized rosette nanotubes in Tet Lett 2012, 53, 1645-1651, International Journal of Pharmaceutics, 2002, 248, 173-182. P. Winnard et al. describe a two step preparation and use of NHS-MAG3 for Technetium-99m labeling of DNA in Nuclear Medicine & Biology, Vol. 24, pp. 425-432, 1997.

Alsbaiee and Winnard fail to disclose the synthesis of rhenium chelated MAG3 oligonucleotides.

The inventors found a novel process for the synthesis of rhenium chelated MAG3 and rhenium chelated MAG3 oligonucleotides.

SUMMARY OF THE INVENTION

In a first aspect, the invention relates to a novel process for preparing a rhenium chelated MAG3 compound of formula (III) in a one pot reaction:

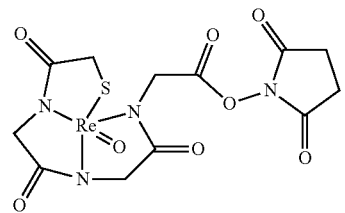

In a second aspect the invention relates to a novel process for preparing a rhenium chelated MAG3 oligonucleotide compound of formula (IV):

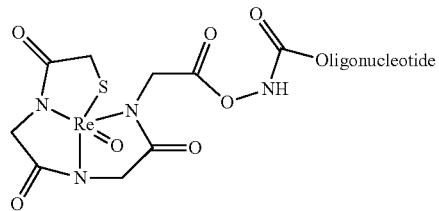

In a third aspect the invention relates to a novel process for preparing a compound of formula (III) or of formula (IV) in a one pot reaction.

Other aspects of the invention will be described more in details hereinbelow.

Definitions

The term "coupling reagent" denote a compound which enables the covalent coupling of two organic molecules such as an carboxylic acid and an amine, alcohol, or thiol. More In the context of the present invention, coupling reagents denote compounds capable of aiding coupling reactions in which a carboxylic acid is coupled to an amine. Coupling reagents are can be used as the water soluble HCl salt. EDC is an example over other carbodiimides. The by-products of EDC is water soluble and can be easily removed through an aqueous work-up. Examples of other coupling reagents is DCC (N,N'-Dicyclohexylcarbodiimide), DIC (N,N'-Diisopropylcarbodiimide), EDC (1-Ethyl-3-(3-dimethylaminopropyl)carbodiimide), EDC-HCl (1-Ethyl-3-(3-dimethylaminopropyl)carbodiimide-HCl), BOP, PyBOP ((benzotriazol-1-yl-oxytripyrrolidinophosphonium hexafluorophosphate), PyBrOP (Bromotripyrrolidinophosphonium hexafluorophosphate), TBTU (2-(1H-Benzotriazole-1-yl)-1,1,3,3-tetramethylaminium tetrafluoroborate), TSTU (N,N,N',N'-Tetramethyl-O—(N-succinimidyl)uronium tetrafluoroborate), TNTU (O-(Bicyclo[2.2.1]hept-5-ene-2,3-dicarboximido)-N,N,N',N'-tetramethyluronium tetrafluoroborate), T3P (2,4,6-Tripropyl-1,3,5,2,4,6-trioxatriphosphorinane-2,4,6-trioxide), HCTU (O-(6-Chlorobenzotriazol-1-yl)-N,N,N',N'-tetramethyluronium hexafluorophosphate), TATU, HATU (N-[(Dimethylamino)-1H-1,2,3-triazolo-[4,5-b]pyridin-1-ylmethylene]-N-methylmethanaminium hexafluorophosphate N-oxide), DMTMM (4-(4,6-Dimethoxy-1,3,5-triazin-2-yl)-4-methylmorpholinium chloride), CDI (1,1'-Carbonyldiimidazole), etc.

The term "alkyl", alone or in combination, signifies a straight-chain or branched-chain alkyl group with 1 to 8 carbon atoms, particularly a straight or branched-chain alkyl group with 1 to 6 carbon atoms and more particularly a straight or branched-chain alkyl group with 1 to 4 carbon atoms. Examples of straight-chain and branched-chain $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, particularly methyl, ethyl, propyl, butyl and pentyl. Particular examples of alkyl are methyl, ethyl and propyl.

The term "amino", alone or in combination, signifies the primary amino group (—$NH_2$), the secondary amino group (—NH—), or the tertiary amino group (—N—).

The term "amino oligonucleotide" denotes an oligonucleotide comprising a non-aromatic $NH_2$. The $NH_2$ group can e.g. be positioned at the 3' or 5' end of the oligonucleotide e.g. 3'oligonucleotide-$CH_2CH_2CH_2CH_2CH_2CH_2$—$NH_2$-5'

The term "amino protecting group" denotes a protecting group of the amino group. Amines are functional groups that often require protecting groups during organic reactions. Carbamates such as t-butoxycarbonyl (Boc, e.g. removed by concentrated strong acid (such as HCl or $CF_3COOH$), or by heating to >80° C.), benzyloxycarbonyl (Cbz, e.g. removed by hydrogenolysis), or 9-fluorenylmethoxycarbonyl (Fmoc e.g. removed by base, such as piperidine) are commonly used amine protecting groups. Additional options for protecting groups with different deprotection conditions can be used, such as described by Peter Wipf, University of Pittsburgh, PA, USA, and colleagues who have developed a useful protecting group for primary, secondary, and heterocyclic amines: 2,2,6,6-tetramethylpiperidin-1-yloxycarbonyl (Tempoc). Acetyl (Ac) group is common in oligonucleotide synthesis for protection of N4 in cytosine and N6 in adenine nucleic bases and can be removed by treatment with a base, most often, with aqueous or gaseous ammonia or methylamine. Ac is too stable to be readily removed from aliphatic amides. Benzoyl (Bz) group is also common in oligonucleotide synthesis for protection of N4 in cytosine and N6 in adenine nucleic bases and is removed by treatment with a base, most often with aqueous or gaseous ammonia or methylamine. Bz is too stable to be readily removed from aliphatic amides. Other suitable amino protecting groups commonly use d can also be considered by the person skilled in the art such as DMF or iBu.

The term "aryl", alone or in combination, denotes a monovalent aromatic carbocyclic mono- or bicyclic ring system comprising 6 to 10 carbon ring atoms, optionally substituted with 1 to 3 substituents independently selected from halogen, hydroxyl, alkyl, alkenyl, alkynyl, alkoxy, alkoxyalkyl, alkenyloxy, carboxyl, alkoxycarbonyl, alkylcarbonyl and formyl. Examples of aryl include phenyl and naphthyl, in particular phenyl.

The term "chelate" denotes the fact that a compound containing a ligand (e.g. organic) bonds to a central metal atom at two or more points. It generally involves the formation or presence of two or more separate coordinate bonds between a polydentate (multiple bonded) ligand and a single central atom. These ligands are called chelants, chelators, chelating agents, or sequestering agents. It is typically a type of bonding of ions and molecules to metal ions. The compound of formula (II) according to the invention is an examples of a chelate or chelate complex.

The chelator moieties of the present invention may comprise a combination of any number of atoms selected from the group consisting of nitrogen atoms, sulfur atoms, oxygen atoms, and phosphorus atoms. In certain particular embodiments, the chelator moiety includes a combination of three to five such atoms. In some embodiments, the chelator is capable of chelating to any number of valent metal ions through coordination to other atoms, such as nitrogen atoms, sulfur atoms, oxygen atoms, and/or phosphorus atoms. In certain embodiments, the chelator is capable of chelating three to five valent metal ions. Any valent metal ion is contemplated for chelation to the chelators of the present invention. Examples of these valent metal ions include, but are not limited to, 186Re, 188Re, Tc-99m, Cu-60, Cu-61, Cu-62, In-111, T1-201, Ga-67, and Ga-68.

The terms "halogen" or "halo", alone or in combination, signifies fluorine, chlorine, bromine or iodine and particularly fluorine, chlorine or bromine, more particularly fluorine. The term "halo", in combination with another group, denotes the substitution of said group with at least one halogen, particularly substituted with one to five halogens, particularly one to four halogens, i.e. one, two, three or four halogens.

The terms "thiol" signify the —SH group.

"Thiol protecting group" is a protecting group of the thiol group and is also used to protect hydroxyl groups. Examples of hydroxyl protecting groups are acetyl (Ac), benzoyl (Bz), benzyl (Bn), β-methoxyethoxymethyl ether (MEM), dimethoxytrityl (or bis-(4-methoxyphenyl)phenylmethyl) (DMT), trimethoxytrityl (or tris-(4-methoxyphenyl)phenylmethyl) (TMT), methoxymethyl ether (MOM), methoxytrityl [(4-methoxyphenyl)diphenylmethyl (MMT), p-methoxybenzyl ether (PMB), methylthiomethyl ether, pivaloyl (Piv), tetrahydropyranyl (THP), tetrahydrofuran (THF), trityl or triphenylmethyl (Tr), silyl ether (for example trimethylsilyl (TMS), tert-butyldimethylsilyl (TBDMS), tri-iso-propylsilyloxymethyl (TOM) and triisopropylsilyl (TIPS) ethers), methyl ethers and ethoxyethyl ethers (EE). Particular examples of hydroxyl protecting group are DMT and TMT, in particular DMT.

The term "LNA monomer" refers to an LNA nucleotide, meaning a nucleotide for which the nucleoside is an LNA nucleoside as defined herein.

The term "one pot synthesis" denotes a strategy to improve the efficiency of a chemical reaction whereby a reactant is subjected to successive chemical reactions in just one reactor without intermediate separation or purification steps. This is much desired by chemists because avoiding a lengthy separation process and purification of the intermediate chemical compounds can save time and resources while increasing chemical yield.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid, particularly hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein. In addition these salts may be prepared form addition of an inorganic base or an organic base to the free acid. Salts derived from an inorganic base include, but are not limited to, the sodium, potassium, lithium, ammonium, calcium, magnesium salts. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins.

The oligonucleotide of the invention can also be present in the form of zwitterions. Particularly preferred pharmaceutically acceptable salts of the invention are the sodium, lithium, potassium and trialkylammonium salts.

The term "precursor of a rhenium complex" denotes a rhenium atom which can chelate a compound of formula (I). Examples of precursors of a rhenium complex are $ReOCl_3(PPh_3)_2$ (oxotrichlorobis(triphenylphosphine)rhenium(V)) which is commercially available. Other examples are $Re(NPh)Cl_3(PPh_3)_2$, $ReO_2(PPh_3)_2I$, or $Re(NPh)Cl_3(PPh_3)_2$.

The term "protecting group", alone or in combination, signifies a group which selectively blocks a reactive site in a multifunctional compound such that a chemical reaction can be carried out selectively at another unprotected reactive site. Protecting groups can be removed. Exemplary protecting groups are amino-protecting groups, carboxy-protecting groups or hydroxy-protecting groups.

"Phosphate protecting group" is a protecting group of the phosphate group. Examples of phosphate protecting group are 2-cyanoethyl and methyl. A particular example of phosphate protecting group is 2-cyanoethyl.

Rhenium complexes according to the invention are Re(V) complexes.

If one of the starting materials or compounds of the invention contain one or more functional groups which are not stable or are reactive under the reaction conditions of one or more reaction steps, appropriate protecting groups (as described e.g. in "Protective Groups in Organic Chemistry" by T. W. Greene and P. G. M. Wuts, 3$^{rd}$ Ed., 1999, Wiley, New York) can be introduced before the critical step applying methods well known in the art. Such protecting groups can be removed at a later stage of the synthesis using standard methods described in the literature. Examples of protecting groups are tert-butoxycarbonyl (Boc), 9-fluorenylmethyl carbamate (Fmoc), 2-trimethylsilylethyl carbamate (Teoc), carbobenzyloxy (Cbz) and p-methoxybenzyloxycarbonyl (Moz).

The compounds described herein can contain several asymmetric centers and can be present in the form of optically pure enantiomers, mixtures of enantiomers such as, for example, racemates, mixtures of diastereoisomers, diastereoisomeric racemates or mixtures of diastereoisomeric racemates.

Oligonucleotide

The term "oligonucleotide" as used herein is defined as it is generally understood by the skilled person as a molecule comprising two or more covalently linked nucleosides. Such covalently bound nucleosides may also be referred to as nucleic acid molecules or oligomers. Oligonucleotides are commonly made in the laboratory by solid-phase chemical synthesis followed by purification. When referring to a sequence of the oligonucleotide, reference is made to the sequence or order of nucleobase moieties, or modifications thereof, of the covalently linked nucleotides or nucleosides. The oligonucleotide of the invention is man-made, and is chemically synthesized, and is typically purified or isolated. The oligonucleotide of the invention may comprise one or more modified nucleosides or nucleotides.

Antisense Oligonucleotides

The term "Antisense oligonucleotide" as used herein is defined as oligonucleotides capable of modulating expression of a target gene by hybridizing to a target nucleic acid, in particular to a contiguous sequence on a target nucleic acid. The antisense oligonucleotides are not essentially double stranded and are therefore not siRNAs or shRNAs. Preferably, the antisense oligonucleotides of the present invention are single stranded. It is understood that single stranded oligonucleotides of the present invention can form hairpins or intermolecular duplex structures (duplex between two molecules of the same oligonucleotide), as long as the degree of intra or inter self complementarity is less than 50% across of the full length of the oligonucleotide.

Sugar Modifications

The oligomer of the invention may comprise one or more nucleosides which have a modified sugar moiety, i.e. a modification of the sugar moiety when compared to the ribose sugar moiety found in DNA and RNA.

Numerous nucleosides with modification of the ribose sugar moiety have been made, primarily with the aim of improving certain properties of oligonucleotides, such as affinity and/or nuclease resistance.

Such modifications include those where the ribose ring structure is modified, e.g. by replacement with a hexose ring (HNA), or a bicyclic ring, which typically have a biradical bridge between the C2 and C4 carbons on the ribose ring (LNA), or an unlinked ribose ring which typically lacks a bond between the C2 and C3 carbons (e.g. UNA). Other sugar modified nucleosides include, for example, bicyclohexose nucleic acids (WO 2011/017521) or tricyclic nucleic acids (WO 2013/154798). Modified nucleosides also include nucleosides where the sugar moiety is replaced with a non-sugar moiety, for example in the case of peptide nucleic acids (PNA), or morpholino nucleic acids.

Sugar modifications also include modifications made via altering the substituent groups on the ribose ring to groups other than hydrogen, or the 2'-OH group naturally found in DNA and RNA nucleosides. Substituents may, for example be introduced at the 2', 3', 4' or 5' positions.

2' Sugar Modified Nucleosides.

A 2' sugar modified nucleoside is a nucleoside which has a substituent other than H or —OH at the 2' position (2' substituted nucleoside) or comprises a 2' linked biradical capable of forming a bridge between the 2' carbon and a second carbon in the ribose ring, such as LNA (2'-4' biradical bridged) nucleosides.

Indeed, much focus has been spent on developing 2' modified nucleosides, and numerous 2' modified nucleosides have been found to have beneficial properties when incorporated into oligonucleotides. For example, the 2' modified sugar may provide enhanced binding affinity and/or increased nuclease resistance to the oligonucleotide. Examples of 2' substituted modified nucleosides are 2'-O-alkyl-RNA, 2'-O-methyl-RNA, 2'-alkoxy-RNA, 2'-O-methoxyethyl-RNA (MOE), 2'-amino-DNA, 2'-fluoro-RNA and 2'-F-ANA nucleoside. Further examples can be found in e.g. Freier & Altmann; Nucl. Acid Res., 1997, 25, 4429-4443 and Uhlmann; Curr. Opinion in Drug Development, 2000, 3(2), 293-213 and Deleavey and Damha, Chemistry and Biology 2012, 19, 937. Below are illustrations of some 2' substituted modified nucleosides.

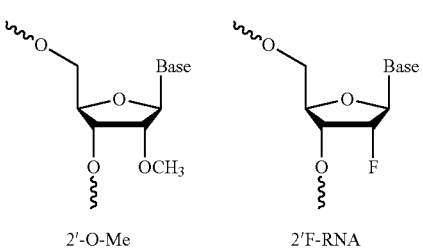

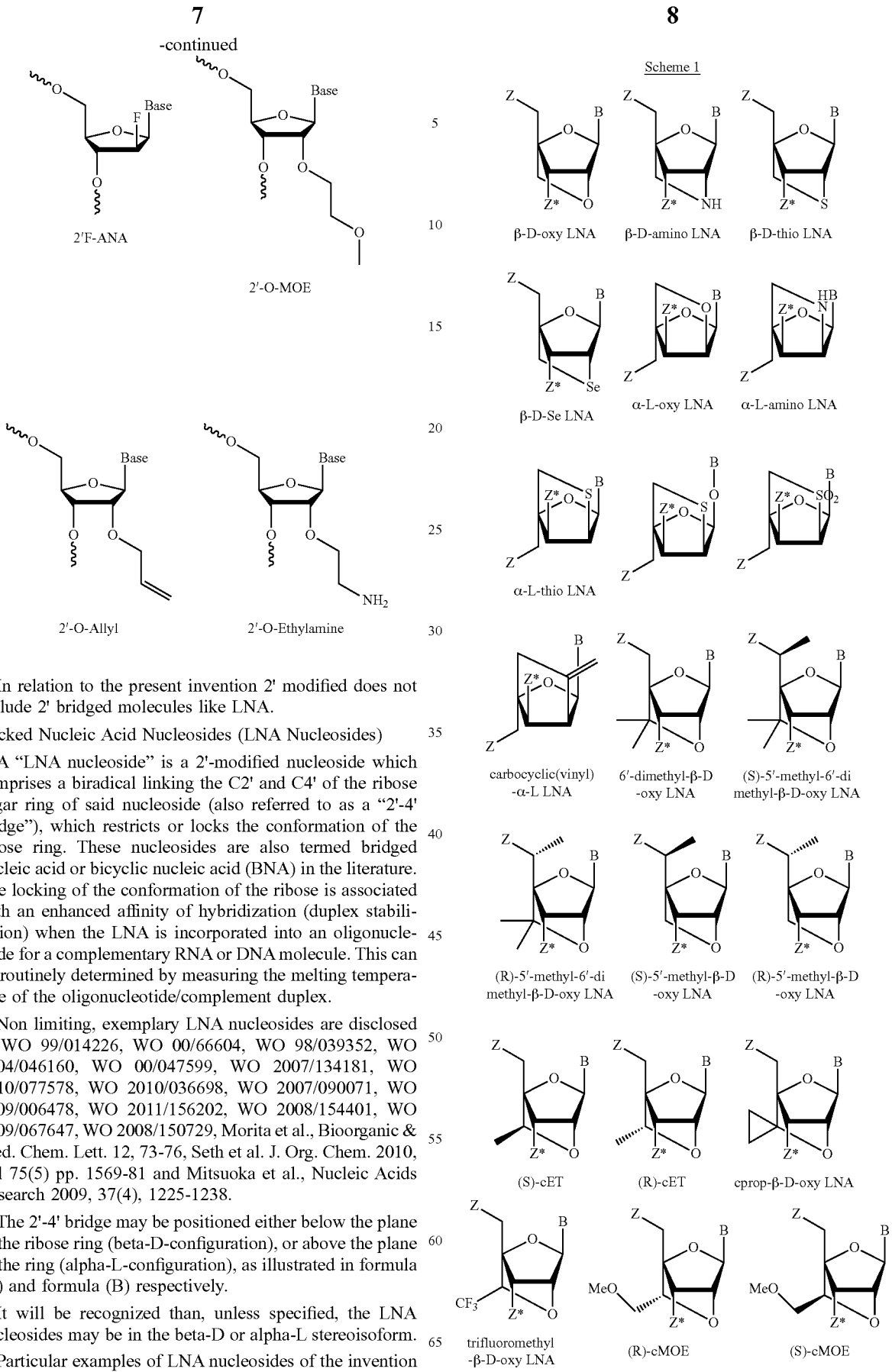

In relation to the present invention 2' modified does not include 2' bridged molecules like LNA.

Locked Nucleic Acid Nucleosides (LNA Nucleosides)

A "LNA nucleoside" is a 2'-modified nucleoside which comprises a biradical linking the C2' and C4' of the ribose sugar ring of said nucleoside (also referred to as a "2'-4' bridge"), which restricts or locks the conformation of the ribose ring. These nucleosides are also termed bridged nucleic acid or bicyclic nucleic acid (BNA) in the literature. The locking of the conformation of the ribose is associated with an enhanced affinity of hybridization (duplex stabilization) when the LNA is incorporated into an oligonucleotide for a complementary RNA or DNA molecule. This can be routinely determined by measuring the melting temperature of the oligonucleotide/complement duplex.

Non limiting, exemplary LNA nucleosides are disclosed in WO 99/014226, WO 00/66604, WO 98/039352, WO 2004/046160, WO 00/047599, WO 2007/134181, WO 2010/077578, WO 2010/036698, WO 2007/090071, WO 2009/006478, WO 2011/156202, WO 2008/154401, WO 2009/067647, WO 2008/150729, Morita et al., Bioorganic & Med. Chem. Lett. 12, 73-76, Seth et al. J. Org. Chem. 2010, Vol 75(5) pp. 1569-81 and Mitsuoka et al., Nucleic Acids Research 2009, 37(4), 1225-1238.

The 2'-4' bridge may be positioned either below the plane of the ribose ring (beta-D-configuration), or above the plane of the ring (alpha-L-configuration), as illustrated in formula (A) and formula (B) respectively.

It will be recognized than, unless specified, the LNA nucleosides may be in the beta-D or alpha-L stereoisoform.

Particular examples of LNA nucleosides of the invention are presented in Scheme 1 (wherein B is as defined above).

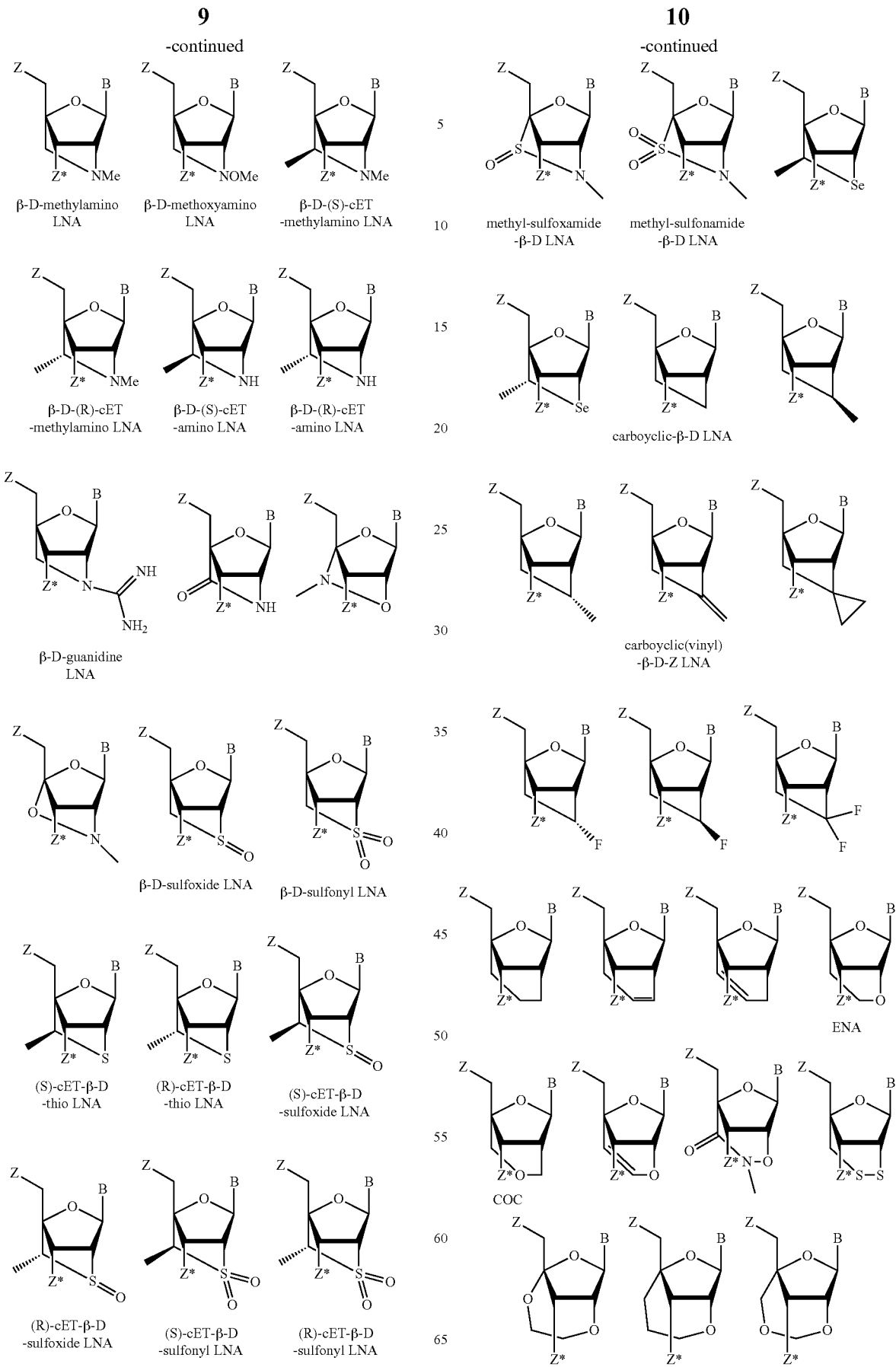

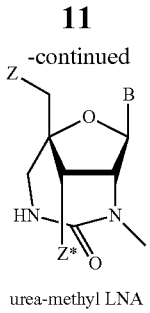

urea-methyl LNA

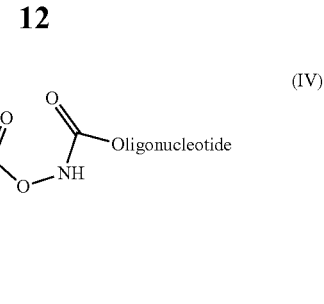

Particular LNA nucleosides are beta-D-oxy-LNA, 6'-methyl-beta-D-oxy LNA such as (S)-6'-methyl-beta-D-oxy-LNA ((S)-cET) and ENA.

DETAILED DESCRIPTION OF THE INVENTION

In one aspect, the invention relates to a method for preparing a compound of formula (III) comprising the step of:

a) Reacting a compound of formula (I):

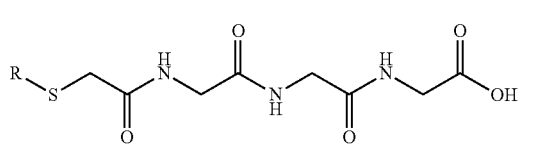

wherein R is H or a thiol protecting group,
with a precursor of a rhenium complex in a solvent to obtain a compound of formula (II):

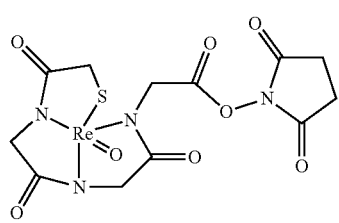

b) Adding N-hydroxysuccinimide with a coupling reagent to obtain a compound of formula (III):

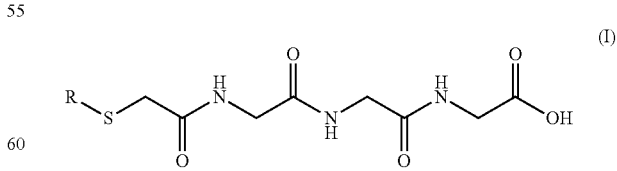

wherein steps a) and b) are performed in a one pot reaction.

In an embodiment of the method of the invention, there is a further step c) of adding an amino oligonucleotide with a base to obtain a compound of formula (IV):

(IV)

Oligonucleotide structure

In an embodiment of the method of the invention, steps a) and b) are performed in a one pot synthesis. In an embodiment, steps a), b) and c) are performed in a one pot synthesis.

In an embodiment of the method of the invention, the precursor of a rhenium complex is selected from the group consisting of $ReOCl_3(PPh_3)_2$, $Re(NPh)Cl_3(PPh_3)_2$, $ReO_2(PPh_3)_2I$, and $Re(NPh)Cl_3(PPh_3)_2$.

In an embodiment of the method of the invention the precursor of a rhenium complex is $ReOCl_3(PPh_3)_2$.

In an embodiment of the method of the invention R is H.

In an embodiment of the method of the invention R is a thiol protecting group selected from the group consisting of acetyl (Ac), benzoyl (Bz), benzyl (Bn), (3-methoxyethoxymethyl ether (MEM), dimethoxytrityl (or bis-(4-methoxyphenyl)phenylmethyl) (DMT), trimethoxytrityl (or tris-(4-methoxyphenyl)phenylmethyl) (TMT), methoxymethyl ether (MOM), methoxytrityl [(4-methoxyphenyl)diphenylmethyl (MMT), p-methoxybenzyl ether (PMB), methylthiomethyl ether, pivaloyl (Piv), tetrahydropyranyl (THP), tetrahydrofuran (THF), trityl or triphenylmethyl (Tr), silyl ether (for example trimethylsilyl (TMS), tert-butyldimethylsilyl (TBDMS), tri-iso-propylsilyloxymethyl (TOM) and triisopropylsilyl (TIPS) ethers), and methyl ethers and ethoxyethyl ethers (EE).

In an embodiment of the method of the invention R is a thiol protecting group selected from the group consisting of acetyl (Ac) and benzoyl (Bz).

In an embodiment of the method of the invention the solvent in step a) is a mixture of a polar aprotic solvent and of a polar protic solvent. In an embodiment of the method of the invention the solvent is a mixture of DMF and MeOH. In an embodiment of the method of the invention, the solvent is a mixture of DMF and MeOH of an about 1:1 volume ratio.

In an embodiment of the method of the invention a base is further used in step a). In an embodiment of the method of the invention the base is NaOMe.

In an embodiment, the method of the invention comprises the steps of:

c) Reacting a compound of formula (I):

(I)

wherein R is H or a thiol protecting group selected from the group consisting of acetyl (Ac) and benzoyl (Bz), with $ReOCl_3(PPh_3)_2$,
in DMF:MeOH in an about 1:1 volume ratio to obtain a compound of formula (II):

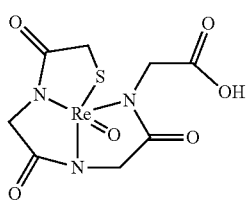

d) Adding N-hydroxysuccinimide with EDC-HCl to obtain a compound of formula (III):

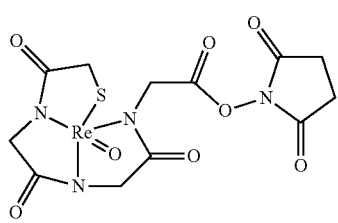

c) Adding an amino oligonucleotide with a base to obtain a compound of formula (IV):

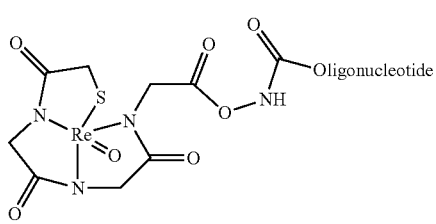

wherein the oligonucleotide comprises at least one 2' sugar modified nucleoside or LNA nucleoside In an embodiment, the method of the invention the oligonucleotide is an antisense oligonucleotide. In an embodiment, the method of the invention the antisense oligonucleotide contains a 2' sugar modified nucleoside or LNA nucleoside as defined herein.

MAG3 is commercially available from usual vendors, e.g. Sigma Aldrich or ABX. The compound of formula (I) can be commercially available, for example as NHS-MAG3 acetyl protected from various vendors such as Sigma Aldrich (Nature protocols 2007-4-21, Yi Wang et al.)

Unless stated otherwise, all starting products, reagents and solvents are commercially available.

In step b) a solvent is used. It can be a polar aprotic solvent, a polar protic solvent or mixtures thereof.

Examples of polar aprotic solvents are DCM (dichloromethane), N-methylpyrrolidone, THF (tetrahydrofurane), ETOAc (ethyl acetate), acetone, DMF (dimethylformamide), MeCN (acetonitrile), DMSO (dimethyl sulfoxide) and PC (propylene carbonate) or mixtures thereof.

In one or all embodiments of the method of the invention, the polar aprotic solvent is DMF.

Examples of polar protic solvents are formic acid, n-butanol, IPA (isopropanol), EtOH (ethanol), MeOH (methanol), AcOH (acetic acid) and water or mixtures thereof.

In one or all embodiments of the method of the invention, the polar protic solvent is MeOH.

In one or all embodiments of the method of the invention, the solvent can be a mixture of a polar aprotic solvent and of a polar protic solvent, for example DMF:MeOH, for example DMF:MeOH in an about 1:1 volume ratio.

In step c) a solvent can be used. In an embodiment, N-(3-Dimethylaminopropyl)-N'-ethylcarbodiimide hydrochloride is used.

The coupling reagent of step b) can be selected from the group consisting of coupling reagents is DCC (N,N'-Dicyclohexylcarbodiimide), DIC (N,N'-Diisopropylcarbodiimide), EDC (1-Ethyl-3-(3-dimethylaminopropyl)carbodiimide), EDC-HCl (1-Ethyl-3-(3-dimethylaminopropyl) carbodiimide-HCl), BOP, PyBOP ((benzotriazol-1-yloxytripyrrolidinophosphonium hexafluorophosphate), PyBrOP (Bromotripyrrolidinophosphonium hexafluorophosphate), TBTU (2-(1H-Benzotriazole-1-yl)-1,1,3,3-tetramethylaminium tetrafluoroborate), TSTU (N,N,N',N'-Tetramethyl-O—(N-succinimidyl)uronium tetrafluoroborate), TNTU (O-(Bicyclo[2.2.1]hept-5-ene-2,3-dicarboximido)-N,N,N',N'-tetramethyluronium tetrafluoroborate), T3P (2,4,6-Tripropyl-1,3,5,2,4,6-trioxatriphosphorinane-2,4,6-trioxide), HCTU (O-(6-Chlorobenzotriazol-1-yl)-N,N,N',N'-tetramethyluronium hexafluorophosphate), TATU, HATU (N-[(Dimethylamino)-1H-1,2,3-triazolo-[4,5-b]pyridin-1-ylmethylene]-N-methylmethanaminium hexafluorophosphate N-oxide) and DMTMM (4-(4,6-Dimethoxy-1,3,5-triazin-2-yl)-4-methylmorpholiniumchloride), CDI (1,1'-Carbonyldiimidazole).

In an embodiment of the method of the invention, the coupling reagent is EDC-HCl (1-Ethyl-3-(3-dimethylaminopropyl)carbodiimide-HCl).

The method of the invention can be implemented in the following non-limiting embodiments:

1. A method for preparing a compound of formula (III) comprising the step of:

a) Reacting a compound of formula (I):

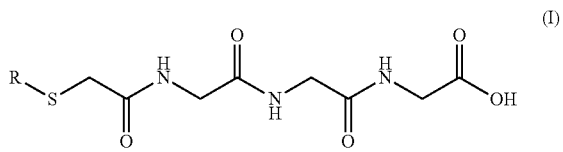

wherein R is H or a thiol protecting group, with a precursor of a rhenium complex in a solvent to obtain a compound of formula (II):

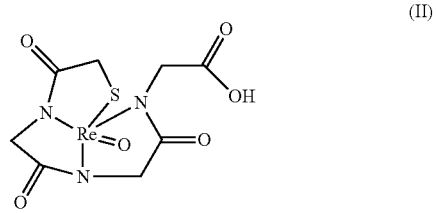

b) Adding N-hydroxysuccinimide with a coupling reagent to obtain a compound of formula (III):

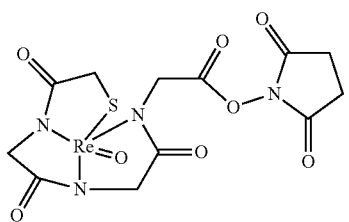

(III)

wherein steps a) and b) are performed in a one pot reaction.

2. The method of embodiment 1, further comprising the step c) of adding an amino oligonucleotide with a base to obtain a compound of formula (IV):

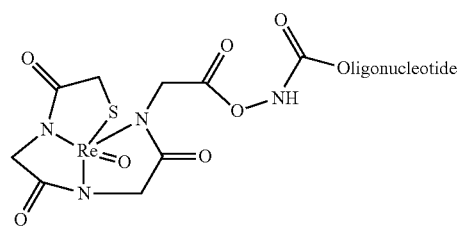

(IV)

3. The method of embodiment 2, wherein steps a), b) and c) are performed in a one pot synthesis.

4. The method of any one of embodiments 1 to 3, wherein the precursor of a rhenium complex is selected from the group consisting of ReOCl$_3$(PPh$_3$)$_2$, Re(NPh)Cl$_3$(PPh$_3$)$_2$, ReO$_2$(PPh$_3$)$_2$I, and Re(NPh)Cl$_3$(PPh$_3$)$_2$.

5. The method of embodiment 4, wherein the precursor of a rhenium complex is ReOCl$_3$(PPh$_3$)$_2$.

6. The method of any one of embodiments 1 to 5, wherein R is H.

7. The method of any one of embodiments 1 to 5, wherein R is a thiol protecting group selected from the group consisting of acetyl (Ac), benzoyl (Bz), benzyl (Bn), (3-methoxyethoxymethyl ether (MEM), dimethoxytrityl (or bis-(4-methoxyphenyl)phenylmethyl) (DMT), trimethoxytrityl (or tris-(4-methoxyphenyl)phenylmethyl) (TMT), methoxymethyl ether (MOM), methoxytrityl [(4-methoxyphenyl)diphenylmethyl (MMT), p-methoxybenzyl ether (PMB), methylthiomethyl ether, pivaloyl (Piv), tetrahydropyranyl (THP), tetrahydrofuran (THF), trityl or triphenylmethyl (Tr), silyl ether (for example trimethylsilyl (TMS), tert-butyldimethylsilyl (TBDMS), tri-iso-propylsilyloxymethyl (TOM) and triisopropylsilyl (TIPS) ethers), and methyl ethers and ethoxyethyl ethers (EE).

8. The method of embodiment 6 or 7, wherein R is a thiol protecting group selected from the group consisting of acetyl (Ac) and benzoyl (Bz).

9. The method of any one of embodiments 1 to 8, wherein the solvent in step a) is a mixture of a polar aprotic solvent and of a polar protic solvent.

10. The method of embodiment 8, wherein the DMF:MeOH in an about 1:1 volume ratio.

11. The method of any one of embodiments 1 to 10, wherein a base is further used in step a).

12. The method of embodiment 11, wherein the base is NaOMe.

13. The method of any one of embodiments 1 to 12 comprising the steps of:

a) Reacting a compound of formula (I):

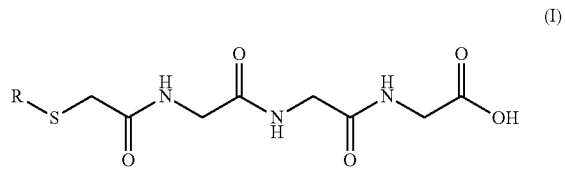

(I)

wherein R is a thiol protecting group selected from the group consisting of acetyl (Ac) and benzoyl (Bz), with ReOCl$_3$(PPh$_3$)$_2$,
in DMF:MeOH in an about 1:1 volume ratio to obtain a compound of formula (II):

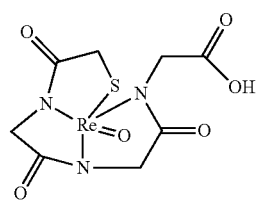

(II)

b) Adding N-hydroxysuccinimide with EDC-HCl to obtain a compound of formula (III):

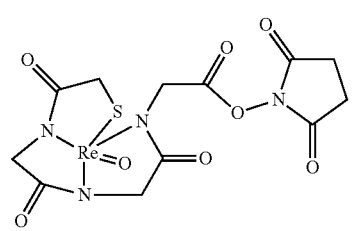

(III)

c) Adding an amino oligonucleotide with a base to obtain a compound of formula (IV):

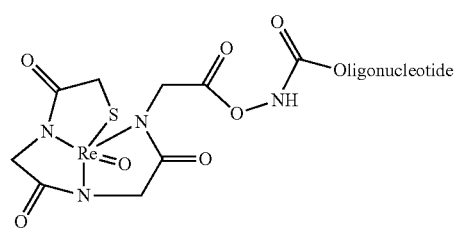

(IV)

wherein the oligonucleotide comprises at least one 2' sugar modified nucleoside or LNA nucleoside and wherein steps a), b) and c) are performed in a one pot reaction.

14. The method of any one of embodiments 1 to 13, wherein the oligonucleotide is an antisense oligonucleotide.

15. The method of embodiment 14, wherein the antisense oligonucleotide comprises at least one 2' sugar modified nucleoside or LNA nucleoside.

16. The method of any one of embodiments 1 to 15 wherein the coupling reagent is selected from the group consisting of coupling reagents is DCC (N,N'-Dicyclohexylcarbodiimide), DIC (N,N'-Diisopropylcarbodiimide), EDC (1-Ethyl-3-(3-dimethylaminopropyl)carbodiimide), EDC-HCl (1-Ethyl-3-(3-dimethylaminopropyl)carbodiimide-HCl), BOP, PyBOP ((benzotriazol-1-yl-oxytripyrrolidinophosphonium hexafluorophosphate), PyBrOP (Bromotripyrrolidinophosphonium hexafluorophosphate), TBTU (2-(1H-Benzotriazole-1-yl)-1,1,3,3-tetramethylaminium tetrafluoroborate), TSTU (N,N,N',N'-Tetramethyl-O—(N-succinimidyl)uronium tetrafluoroborate), TNTU (O-(Bicyclo[2.2.1]hept-5-ene-2,3-dicarboximido)-N,N,N',N'-tetramethyluronium tetrafluoroborate), T3P (2,4,6-Tripropyl-1,3,5,2,4,6-trioxatriphosphorinane-2,4,6-trioxide), HCTU (O-(6-Chlorobenzotriazol-1-yl)-N,N,N',N'-tetramethyluronium hexafluorophosphate), TATU, HATU (N-[(Dimethylamino)-1H-1,2,3-triazolo-[4,5-b]pyridin-1-ylmethylene]-N-methylmethanaminium hexafluorophosphate N-oxide) and DMTMM (4-(4,6-Dimethoxy-1,3,5-triazin-2-yl)-4-methylmorpholiniumchloride), CDI (1,1'-Carbonyldiimidazole).

17. The method of embodiment 16, wherein the coupling reagent is EDC-HCl (1-Ethyl-3-(3-dimethylaminopropyl)carbodiimide-HCl).

EXAMPLE

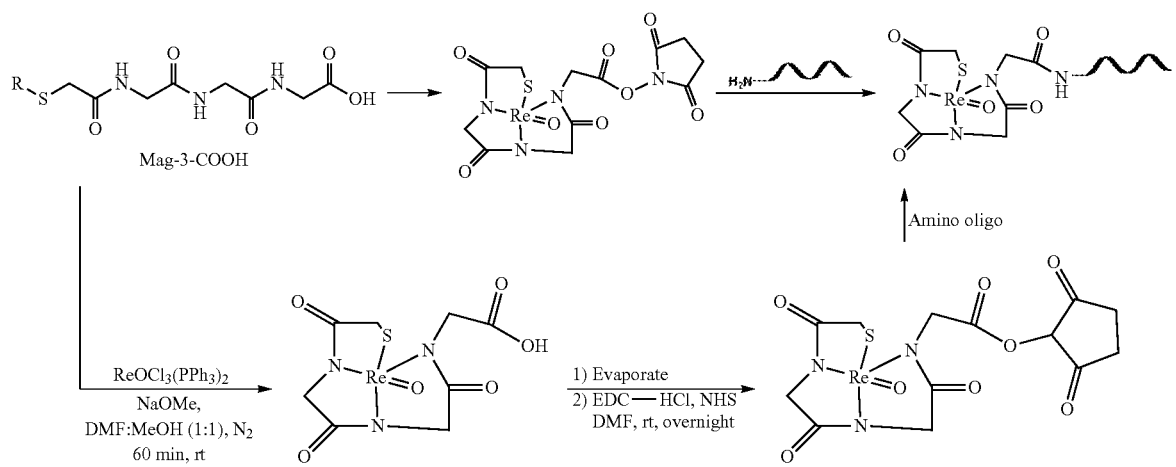

Degassed (N$_2$ and/or argon) DMF:MeOH (2.5 mL, ratio 1:1) was added to a flask containing protected Mag-3-COOH (10 mg, 27 umol), ReOCl$_3$(PPh$_3$)$_2$ (45 mg, 54 umol), and NaOMe (29.4 mg, 554 umol). The resulting solution was then stirred for 60 min. Hereafter, the reaction mixture was evaporated to approximately 0.5 mL volume using a stream of N$_2$. Then, N-hydroxysuccinimide (9.4 mg, 82 umol) and EDC-HCl (6.3 mg, 33 umol) was added and the resulting mixture was left to stir overnight. After reacting overnight the mixture was diluted w. 0.5 mL DMSO and stirred for 15 min. Then the amino-modified oligonucleotide (30 mg dissolved in 0.5 mL NaHCO$_3$ pH=8.5) was added. The resulting mixture was stirred overnight in order to afford the wanted oligonucleotide compound (i.e. amino oligonucleotide conjugated to Mag-3 chelated with rhenium).

Purification: The oligonucleotide was precipitated from the one-pot reaction by adding a solution of 2% LiClO$_4$ in acetone to the above reaction mixture. Then the flask was swirled, centrifuged, and decanted. The residue remaining (precipitated oligonucleotide) was then dissolved in water and purified by reverse phase HPLC.

The invention claimed is:
1. A method for preparing a compound of formula (III) comprising the step of:
a) reacting a compound of formula (I):

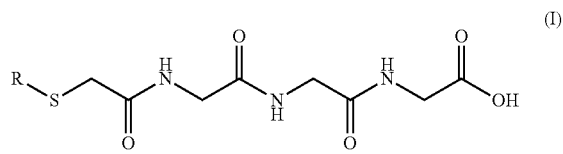

wherein R is H or a thiol protecting group, with a precursor of a rhenium complex in a solvent to obtain a compound of formula (II):

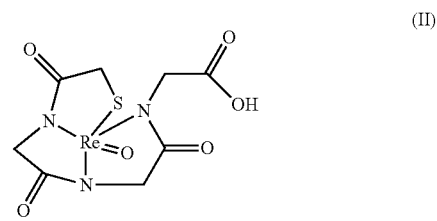

b) adding N-hydroxysuccinimide with a coupling reagent to obtain a compound of formula (III):

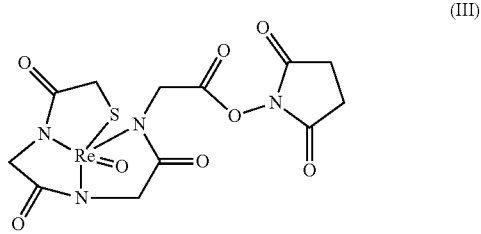

wherein steps a) and b) are performed in a one pot reaction.

2. The method of claim 1, further comprising the step c) of adding an amino oligonucleotide with a base to obtain a compound of formula (IV):

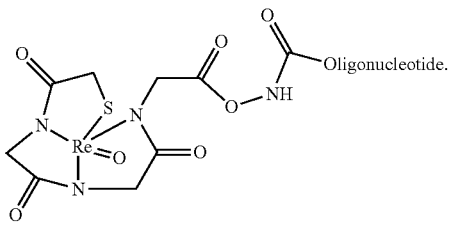
(IV)

3. The method of claim 2, wherein steps a), b) and c) are performed in a one pot reaction.

4. The method of claim 1, wherein the precursor of a rhenium complex is selected from the group consisting of ReOCl$_3$(PPh$_3$)$_2$, Re(NPh)Cl$_3$(PPh$_3$)$_2$, ReO$_2$(PPh$_3$)$_2$I, and Re(NPh)Cl$_3$(PPh$_3$)$_2$.

5. The method of claim 4, wherein the precursor of a rhenium complex is ReOCl$_3$(PPh$_3$)$_2$.

6. The method of claim 1, wherein R is a thiol protecting group selected from the group consisting of acetyl (Ac), benzoyl (Bz), benzyl (Bn), β-methoxyethoxymethyl ether (MEM), dimethoxytrityl (or bis-(4-methoxyphenyl)phenylmethyl) (DMT), trimethoxytrityl (or tris-(4-methoxyphenyl) phenylmethyl) (TMT), methoxymethyl ether (MOM), methoxytrityl [(4-methoxyphenyl)diphenylmethyl (MMT), p-methoxybenzyl ether (PMB), methylthiomethyl ether, pivaloyl (Piv), tetrahydropyranyl (THP), tetrahydrofuran (THF), trityl or triphenylmethyl (Tr), silyl ether (for example trimethylsilyl (TMS), tert-butyldimethylsilyl (TBDMS), tri-iso-propylsilyloxymethyl (TOM) and triisopropylsilyl (TIPS) ethers), and methyl ethers and ethoxyethyl ethers (EE).

7. The method of claim 6, wherein R is a thiol protecting group selected from the group consisting of acetyl (Ac) and benzoyl (Bz).

8. The method of claim 1, wherein the solvent in step a) is a mixture of a polar aprotic solvent and of a polar protic solvent.

9. The method of claim 8, wherein the DMF:MeOH in an about 1:1 volume ratio.

10. The method of claim 1, wherein a base is further used in step a).

11. The method of claim 10, wherein the base is NaOMe.

12. The method of claim 1, comprising the steps of:
a) Reacting a compound of formula (I):

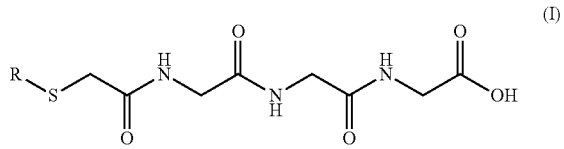
(I)

wherein R is H or a thiol protecting group selected from the group consisting of acetyl (Ac) and benzoyl (Bz), with ReOCl$_3$(PPh$_3$)$_2$, in DMF:MeOH in an about 1:1 volume ratio to obtain a compound of formula (II):

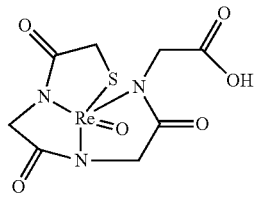
(II)

b) Adding N-hydroxysuccinimide with EDC-HCl to obtain a compound of formula (III):

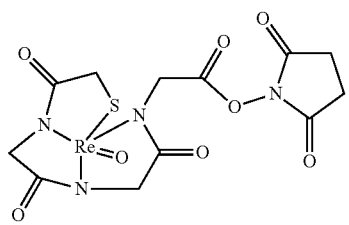
(III)

c) Adding an amino oligonucleotide with a base to obtain a compound of formula (IV):

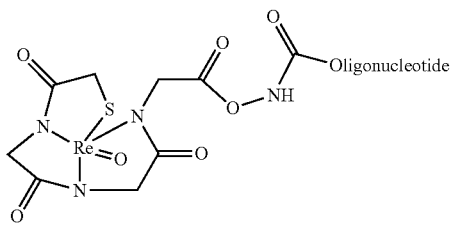
(IV)

wherein the oligonucleotide comprises at least one 2' sugar modified nucleoside or LNA nucleoside and wherein steps a), b) and c) are performed in a one pot reaction.

13. The method of claim 12, wherein the oligonucleotide is an antisense oligonucleotide.

14. The method of claim 13, wherein the antisense oligonucleotide comprises at least one 2' sugar modified nucleoside or LNA nucleoside.

15. The method of claim 1, wherein the coupling reagent is selected from the group consisting of coupling reagents is DCC (N,N'-Dicyclohexylcarbodiimide), DIC (N,N'-Diisopropylcarbodiimide), EDC (1-Ethyl-3-(3-dimethylaminopropyl)carbodiimide), EDC-HCl (1-Ethyl-3-(3-dimethylaminopropyl)carbodiimide-HCl), BOP, PyBOP ((benzotriazol-1-yl-oxytripyrrolidinophosphonium hexafluorophosphate), PyBrOP (Bromotripyrrolidinophosphonium hexafluorophosphate), TBTU (2-(1H-Benzotriazole-1-yl)-1,1,3,3-tetramethylaminium tetrafluoroborate), TSTU (N,N,N',N'-Tetramethyl-O—(N-succinimidyl)uronium tetrafluoroborate), TNTU (O-(Bicyclo[2.2.1]hept-5-ene-2,3-dicarboximido)-N,N,N',N'-tetramethyluronium tetrafluoroborate), T3P (2,4,6-Tripropyl-1,3,5,2,4,6-trioxatriphosphorinane-2,4,6-trioxide), HCTU (O-(6-Chlorobenzotriazol-1-yl)-N,N,N',N'-tetramethyluronium hexafluorophosphate), TATU, HATU (N-[(Dimethylamino)-1H-1,2,3-triazolo-[4,5-b]pyridin-1-ylmethylene]-N-methylmethanaminium hexafluorophosphate N-oxide) and DMTMM (4-(4,6-Dimethoxy-1,3,5-triazin-2-yl)-4-methyl-morpholinium chloride), CDI (1,1'-Carbonyldiimidazole).

16. The method of claim 15, wherein the coupling reagent is EDC-HCl (1-Ethyl-3-(3-dimethylaminopropyl)carbodiimide-HCl).

17. The method of claim 14, wherein the LNA nucleoside is beta-D-oxy-LNA, (S)-6'-methyl-beta-D-oxy-LNA ((S)-CET) and ENA.

* * * * *